Nov. 4, 1958 J. D. SIEBENTHALER Plant Pat. 1,768
ASH TREE
Filed March 26, 1958 2 Sheets-Sheet 1
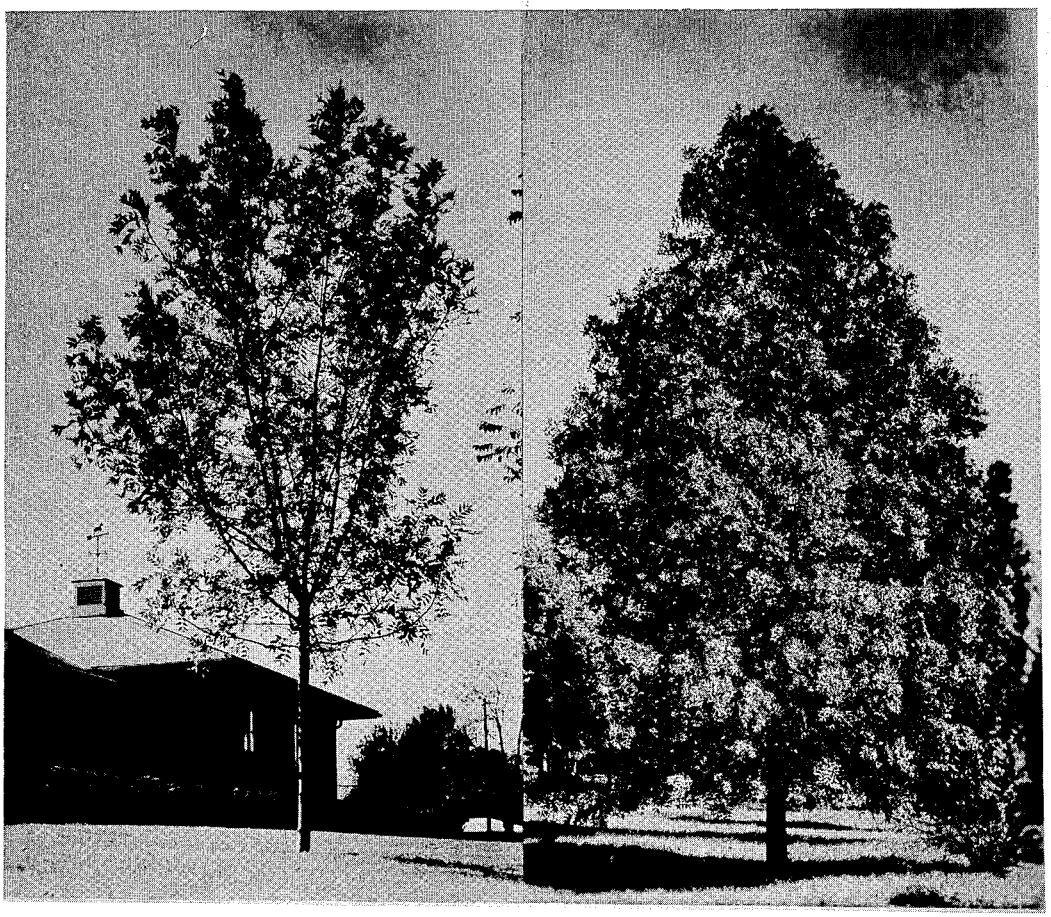
INVENTOR
John D. Siebenthaler
BY Robb & Robb
ATTORNEYS ASH TREE
Filed March 26, 1958 2 Sheets-Sheet 2
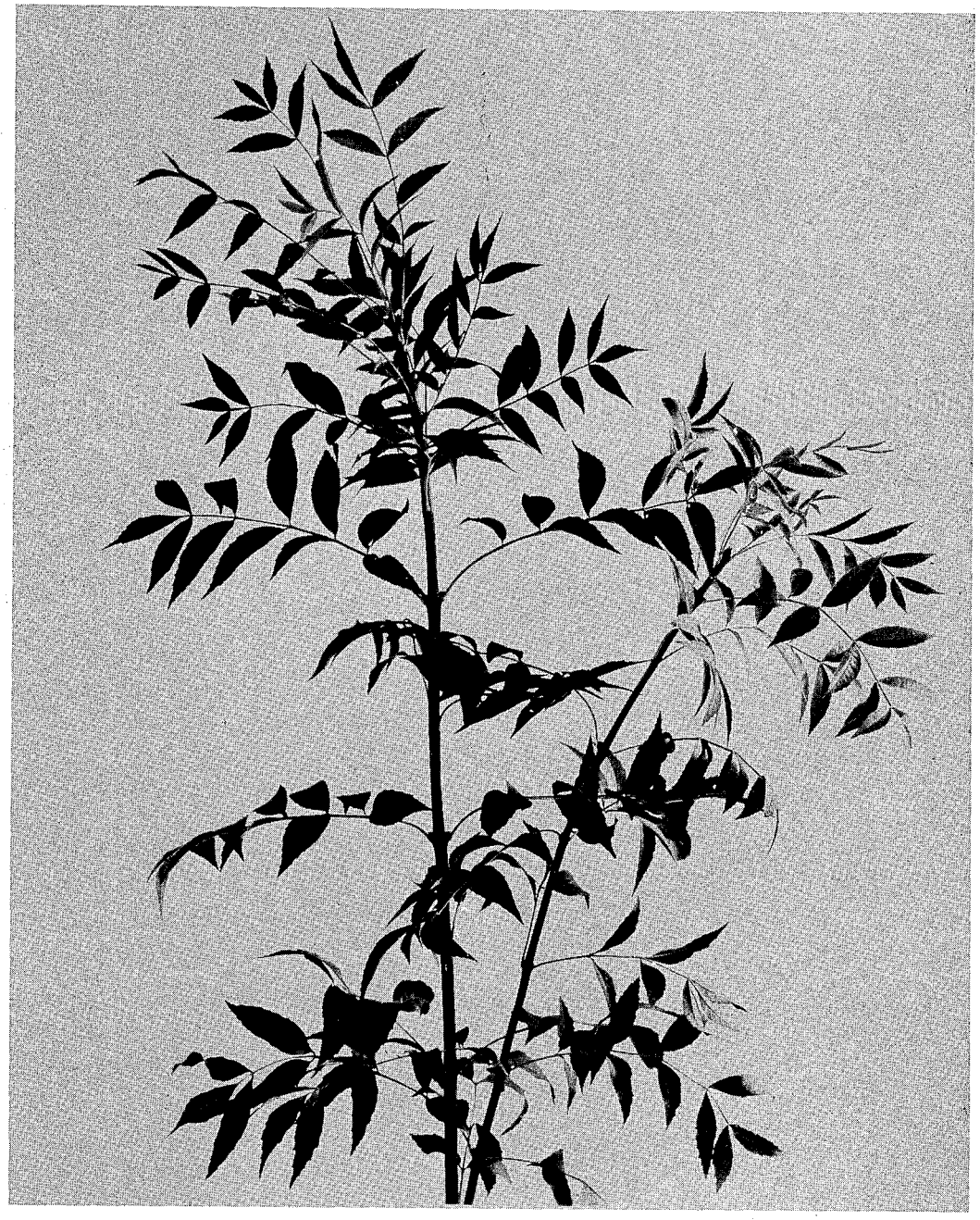
INVENTOR
John D. Siebenthaler
BY Robb & Robb
ATTORNEYS United States Patent Office Plant Pat. 1,768
Patented Nov. 4, 1958

1,768

ASH TREE

John D. Siebenthaler, Dayton, Ohio, assignor to The Siebenthaler Company, Dayton, Ohio, a corporation of Ohio Application March 26, 1958, Serial No. 724,217

1 Claim. (Cl. 47—59)

The present invention relates to a new and distinct variety of ash tree (genus Fraxinus, specie *holotricha*) which was originated by me by selection from seedlings obtained from seeds of the specie aforesaid which I acquired from abroad and which I planted on property being cultivated under my direction and supervision, said property being owned by the assignee hereof and being located at Dayton, Ohio.

It is well known that ash trees are considered useful for street and lawn plantings. However, many specimens have objectionable characteristics which make them undesirable for such use. These objectionable characteristics frequently include rough bark, irregular top formation, heavy fruiting habits, early shedding of foliage, dull color of the foliage, and unduly large size of the mature trees.

The current demand for trees of dwarf and medium sizes makes my new variety most acceptable and commercially valuable because it is particularly characterized by its medium size at maturity, an attractive shape and form in both young and mature stages, a greater foliage persistence later in the autumn season than most ash trees, a habit of bearing very few seeds, attractive bark and foliage, and excellent adaptability to a wide variation of soil conditions.

Asexual reproduction of the new variety by budding, as performed at Dayton, Ohio, shows that the foregoing characteristics and distinctions come true to form and are established and transmitted through succeeding propagations.

The accompanying drawings show typical specimens of both the mature and young trees of my new variety, as well as specimens of the foliage and branches as depicted on a somewhat enlarged scale.

The following is a detailed description of my new variety, with color terminology in accordance with Munsell's Color Chart, except where general color terms of ordinary dictionary significance are obvious:

Locality where grown and observed: Dayton, Ohio.

Tree: Medium size (about 40 feet high at maturity); vigorous; dense; upright; oval-shaped; hardy; sparse bearer.

*Trunk.*— Medium stockiness; medium smoothness.

*Branches.*—Stocky; smooth. Color—gray-green.

*Lenticels.*—Medium number; medium size.

*Leaves.*—Small; about 2½ inches long and about ¾-inch wide; obovate; acutely pointed; medium thickness; smooth; pinnate; opposite; compound of from 5 to 11 leaflets. Color—Moderate Olive Green, Plate 5 GY 4/4 (Munsell). Margin—Finely serrate. Petiole—short; slender. Glands—opposite; small; average 20 in number.

Flowers: Medium blooming period as compared with other varieties.

Dates first and full bloom.—May 15–May 20, respectively.

*Borne.*—In panicles.

*Size.*—Small.

*Color.*—Greenish white.

Fruit:

*Form.*—One-seeded winged samara.

*Peduncle.*—About ⅜-inch long.

*Seed coat.*—About 1¼ inches long and 5/16-inch wide.

Use: As street, lawn and shade tree.

I claim:

A new and distinct variety of ash tree, substantially as herein shown and described, characterized particularly as to novelty by the unique combination of medium size at maturity, attractive shape and form when both young and mature, attractive bark and foliage, persistence of the foliage to later in the autumn season than most ash trees, scant seed production, and excellent adaptability to a wide range of soil conditions.

No references cited.